United States Patent [19]

Inukai et al.

[11] 4,211,666
[45] Jul. 8, 1980

[54] LIQUID CRYSTAL COMPOUNDS

[75] Inventors: Takashi Inukai; Hiromichi Inoue; Hideo Sato, all of Yokohamashi, Japan

[73] Assignee: Chisso Corporation, Osaka, Japan

[21] Appl. No.: 960,710

[22] Filed: Nov. 14, 1978

[30] Foreign Application Priority Data

Nov. 21, 1977 [JP] Japan ............................ 52-139610
Jun. 6, 1978 [JP] Japan ............................ 53-67938

[51] Int. Cl.² ...................... C09K 3/34; C07C 121/64; C02F 1/13
[52] U.S. Cl. ............................ 252/299; 260/465 R; 260/649 R; 568/807; 350/350 R
[58] Field of Search ................... 260/465 R; 252/299; 350/350

[56] References Cited

U.S. PATENT DOCUMENTS

| 3,947,375 | 3/1976 | Gray et al. | 252/299 |
| 4,130,502 | 12/1978 | Eidenschink et al. | 252/299 |

OTHER PUBLICATIONS

Hahn et al., J. Amer. Chem. Soc., vol. 90 (13), p. 3413 (1968).

Primary Examiner—Dolph H. Torrence
Attorney, Agent, or Firm—Fred Philpitt

[57] ABSTRACT

Novel compounds, 4-alkyl-cyclohexenes having at the 1-position thereof p-cyanophenyl group or 4'-cyano-4-biphenylyl group, expressed by the general formula

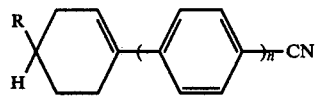

wherein R represents a straight alkyl group having 1~9 carbon atoms and n represents 1 or 2; methods for producing the same; and nematic liquid crystal (L.C.) compositions comprising at least one member selected from the group consisting of said compounds, are provided.

Said compounds having a cyclohexene ring have a lower viscosity than conventional L.C. compounds, and have effectivenesses of short response time when applied to L.C. display apparatus; superior compatibility with other L.C. compounds to form convenient L.C. mixture; and no need of separating cis- and trans-forms in the midway step of the preparation as in the prior art.

6 Claims, No Drawings

LIQUID CRYSTAL COMPOUNDS

DESCRIPTION OF THE INVENTION

The present invention relates to novel compounds of $N_P$ liquid crystal (nematic liquid crystal having a positive dielectric anisotropy).

Recently display apparatuses which utilize liquid crystals have come now into practical use in various fields, and among them, so-called twisted nematic type liquid crystal cells wherein nematic liquid crystals having a positive dielectric anisotropy are employed have come to be most broadly employed. As for characteristic properties required for liquid crystals employed therefor, there are various kinds such as broad temperature range, good stability, low actuation threshold voltage, short response time, etc., but it is difficult for a kind of liquid crystal compound to satisfy all of these requirements. Thus it is the present status that those obtained by admixing various compounds having various characteristic properties together have been put into practical use. The object of the present invention is to provide novel liquid crystal compounds which are useful when employed for such uses.

E. Eidenschink et al have recently reported that 4(trans-4-alkylcyclohexyl)benzonitrile expressed by the following formula (II) is a superior nematic liquid crystal having a low viscosity (Angw. Chem. 89 (1977) p.103):

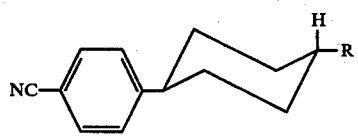

(II)

(wherein R represents a straight chain alkyl group).

However the method for preparing this compound is very complicated. The reason is due to the fact that the alkyl group (R) and the cyanophenyl group are necessarily in the trans-arrangement in the cyclohexane ring in order that this compound takes a liquid crystal state, and thus separation of trans-compound alone is necessary to obtain this compound. According to the above-mentioned report, this compound (II) is obtained by reacting 4-alkylcyclohexanone with phenylmagnesium bromide to synthesize cis- and trans-4-alkylphenylcyclohexanols, separating this cis-compound and trans-compound through chromatography by using silica gel, hydrogenating the resulting cis-compound (wherein R and OH groups are in cis-relation) in the presence of a Raney nickel catalyst, while hydrogenating the resulting trans-compound in the presence of a palladium catalyst, to synthesize the same trans-4-alkyl-1-phenyl-cyclohexane, followed by acetylation, then oxidation according to haloform reaction to form a corresponding carboxylic acid, then amidation and dehydration into a nitrile. The above-mentioned process is expressed by the following equations:

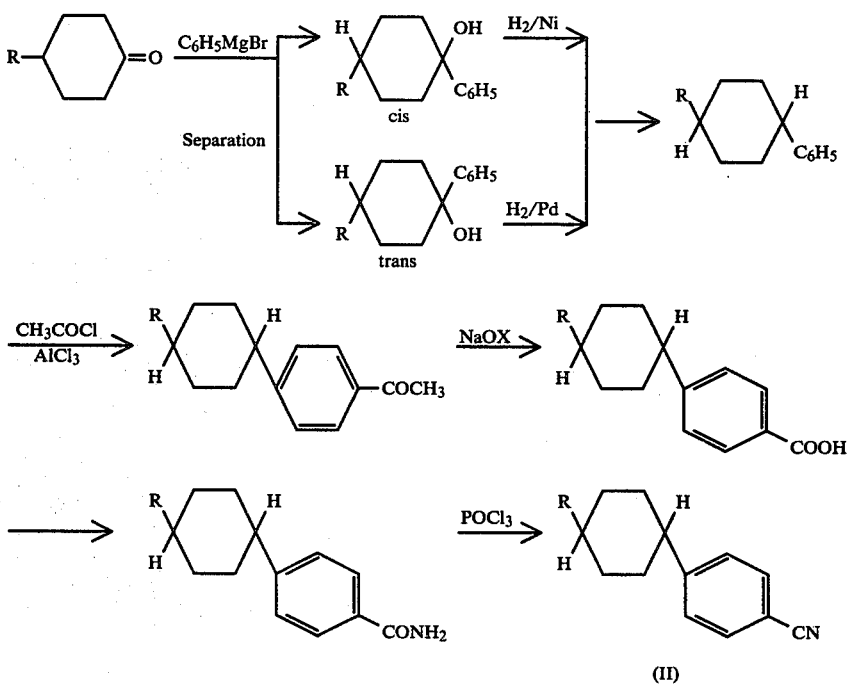

(II)

The inventors of the present invention have found that in case of a compound having a cyclohexene ring, in place of the cyclohexane ring in the above formula (II), a single cyclohexene derivative can be obtained even if a compound in the step of hexanol is dehydrated as it is, without separating cis- and trans-compounds from each other, whereby the preparation becomes very easy and yet the resulting product exhibits a stable liquid crystal state, and have attained the present invention.

The present invention resides firstly in: 1-(p-cyanophenyl)-4-alkylhexenes and 1-(4'-cyano-4-biphenyl)-4-alkylcyclohexenes expressed by the general formula

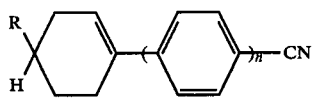

(wherein R represents a straight alkyl group having 1–9 carbon atoms and n represents 1 or 2).

The present invention resides secondly and thirdly in: a method for producing 1-(p-cyanophenyl)-4-alkylhexenes or 1-(4'-cyano-4-biphenyl)-4-alkylcyclohexenes expressed by said formula (I), which comprises reacting a 4-alkylcyclohexanone with p-bromophenylmagnesium bromide or p-bromophenyllithium to prepare a mixture of cis- and trans-forms of 1-(p-bromophenyl)-4-alkylcyclohexanols, or reacting a 4-alkylcyclohexanone with 4-bromo-4'-biphenyllithium to prepare a mixture of cis- and trans-forms of 1-(4'-bromo-4-biphenylyl)-4-alkylcyclohexanols; converting said mixture of cis- and trans-forms into 1-(p-bromophenyl)-4-alkylcyclohexene or 1-(4'-bromo-4-biphenyl)-4-alkylcyclohexene according to a dehydration reaction; and replacing the Br group of said alkylcyclohexene by cyano group.

The present invention resides fourthly in:

A nematic liquid crystal composition containing at least one kind of 1-(p-cyanophenyl)-4-alkylcyclohexene compounds expressed by said formula (I).

The compounds of the formula (I) of the present invention are characterized by having a lower viscosity than conventional liquid crystal compounds, similarly to the compounds of said formula (II) having a cyclohexane ring and this fact results in exhibiting the effect of short response time when they are employed in a liquid crystal display apparatus. Further the compounds of the present invention are a Np liquid crystal, and it is possible to use a mixture of the compounds of this group alone, as it is, for a twisted nematic type liquid crystal cell, and further, since they are superior in the compatibility with other liquid crystal substances such as liquid crystal compounds of azoxybenzene group, those of alkylbiphenyl group, those of cyanophenyl alkylbenzoate group, or the like, it is also possible to use said mixture effectively as a mixed type liquid crystal with these other liquid crystal substances.

Next, the method for preparing the compounds of the formula (I) will be mentioned.

The compounds of the present invention are most preferably prepared according to a following way:

Firstly, a 4-alkylcyclohexanone is reacted with p-bromophenylmagnesium bromide or p-bromophenyllithium to prepare (A) a mixture of cis-forms and trans-forms of 1-(p-bromophenyl)-4-alkylcyclohexanols or a 4-alkylcyclohexanone is reacted with 4-bromo-4'-biphenyllithium to prepare (A) a mixture of cis-form and trans-form of 1-(4'-bromo-4-biphenylyl)-4-alkylcyclohexanols (the first step); and this raw mixture is, as it is, subjected directly to a dehydration reaction to prepare (B) a 1-(p-bromophenyl)-4-alkylcyclohexene or a 1-(4'-bromo-4-biphenylyl)-4-alkylcyclohexene (the second step). This second step is carried out with a good efficiency by heating without any solvent or preferably employing a solvent such as toluene, xylene or the like, in the presence of an acid catalyst such as potassium hydrogen sulfate, oxalic acid, p-toluenesulfonic acid or the like. In this case, since the same alkylcyclohexene (B) is formed from either said cis-form of (A) (A-cis) or said trans-form of (A) (A-trans), it is not necessary at all to separate the cis-form and trans-form from each other at the step of said alkylcyclohexanol. This is one characteristic feature of the preparation method of the present invention. The 4-alkylcyclohexanones as a raw material in this case are obtained by oxidizing a mixture of cis- and trans-forms of 4-alkylcyclohexanols obtained by hydrogenation of a p-alkylphenol, as it is, with anhydrous chromic acid, sodium bichromate or the like. Further, p-bromophenylmagnesium bromide is easily obtained by reacting p-dibromobenzene with an equivalent amount of metallic magnesium, while p-bromophenyllithium or 4'-bromo-4-biphenylyllithium is easily obtained by reacting p-dibromobenzene or 4,4'-dibromobiphenyl with an equivalent amount of n-butyllithium, respectively. The resulting 1-(p-bromophenyl)-4-alkylcyclohexene or 1-(4'-bromo-4-biphenylyl)-4-alkylcyclohexene (B) is reacted with cuprous cyanide in a high boiling solvent, preferably a dipolar aprotic solvent such as N-methyl-2-pyrrolidone, dimethylformamide or the like to obtain the objective 1-(p-cyanophenyl)-4-alkylcyclohexene or 1-(4'-cyano-4-biphenylyl)-4-alkylcyclohexene (I) (the third step). The above process will be shown by the following equations:

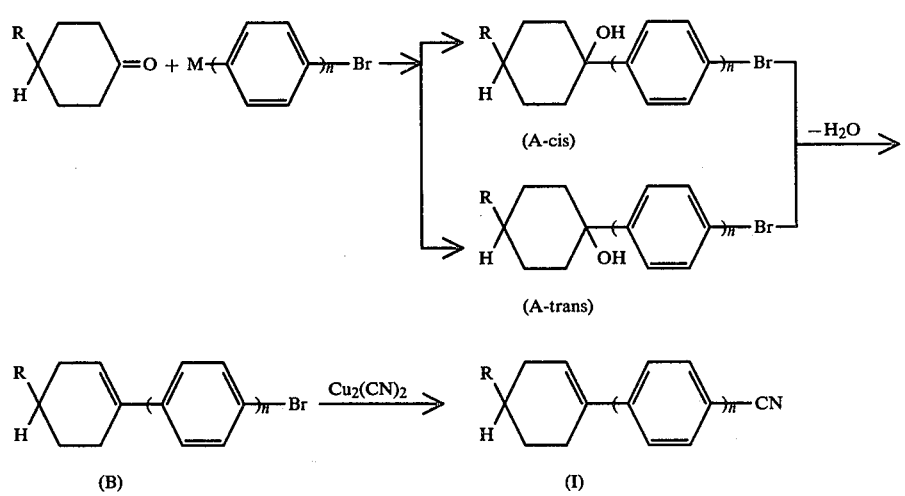

(wherein M represents MgBr or Li and n is 1 or 2).

As for the preparation method of the intermediate (B), there is a following method besides the above-mentioned: a method of reacting an alkylcyclohexanone with phenylmagnesium bromide or phenyllithium to form a 1-phenyl-4-alkylcyclohexanol or a 1-(4-biphenyl)-4-alkylcyclohexanol (both of these hexanols being a mixture of cis- and trans-forms), which is then brominated and further subjected to a dehydration reaction to give said (B). According to this method, however, since the bromination reaction also occurs at other positions than p-position, purification of said compound (B) becomes difficult.

Besides these methods, as for a method for producing said compounds (I) without passing through said intermediate compound (B), there may be considered for example, a course consisting of dehydrating a 1-phenyl-4-alkylcyclohexanol to give a 1-phenyl-4-alkylcyclohexene, which is then acetylated to give a 1-(p-acetylphenyl)-4-alkylcyclohexene, which is then oxidized to give a 1-(p-carboxyphenyl)-4-alkylcyclohexene, followed by converting its carboxyl group into cyano group via carboxyamide group, but since this course takes many stages, there is practically no particular advantage.

The compounds (I) thus obtained have nematic temperature ranges shown in Table 1, and can be employed as a component of the liquid crystal composition used for a twisted nematic type liquid crystal cell.

Table 1

| In (I) | | C-N Point (Melting point) (°C.) | N-I Point (Clear point) (°C.) | |
|---|---|---|---|---|
| n | R | | | |
| 1 | $CH_3$ | 55 (C-I point)** | $(-30)$*** | Example 3 |
| 1 | $C_2H_5$ | 22 (C-I point)** | $(10)$* | Example 1 |
| 1 | $n\text{-}C_3H_7$ | 31 | 44 | Example 4 |
| 1 | $n\text{-}C_4H_9$ | 32.5 | 41.5 | Example 5 |
| 1 | $n\text{-}C_5H_{11}$ | 42 | 57 | Example 2 |
| 1 | $n\text{-}C_6H_{13}$ | 46 | 53.5 | Example 6 |
| 1 | $n\text{-}C_7H_{15}$ | 47.5 | 61 | Example 7 |
| 1 | $n\text{-}C_8H_{17}$ | 32.5 (C-S point) 46 (S-N point) | 60 | Example 8 |
| 2 | $CH_3$ | 157 | 186 | Example 10 |
| 2 | $n\text{-}C_3H_7$ | 110 | 232 | Example 9 |
| 2 | $n\text{-}C_4H_9$ | 113 | 225 | Example 11 |
| 2 | $n\text{-}C_5H_{11}$ | 109 | 225 | Example 12 |

*N-I point of monotropic liquid crystal
**Since these compounds are a monotropic liquid crystal, there is no C-N point.
***Values obtained by extrapolation method.

As seen from the values of the nematic temperature ranges of Table 1, the compounds having a R of $C_2H_5 \sim C_7H_{15}$ among those of $n=1$ in (I) are particularly preferable as a liquid crystal component for liquid crystal display elements, and can be employed as a main component therefor. Further the compounds of $n=2$ exhibit a liquid crystal state in a relatively high temperature range, and are suitable for obtaining liquid crystal compositions having a broad nematic temperature range as shown in the Examples mentioned below, by employing them in admixture with said compounds of $n=1$.

Further the compounds of $n=2$ of (I) serve the purpose of broadening the nematic temperature range of not only those of $n=1$, but also other nematic liquid crystal substances having a positive dielectric anisotropy, when added thereto. As for such other substances, for example, 4-alkyl-4'-cyanobiphenyls, 1-(4-cyanophenyl)-4'-alkylcyclohexanes, 4-alkylbenzoic acid-4'-cyanophenyl esters, 4-alkylbenzylidene-4'-cyanoanilines, etc. are mentioned. Further, by adding them to liquid crystal compounds having a negative dielectric anisotropy but being unsuitable by themselves for twisted nematic type liquid crystal display cell, it is possible to convert them into liquid crystals having a positive dielectric anisotropy (see Example 13 mentioned below).

Next the preparation methods of the compounds of the present invention and examples of their uses will be mentioned in more detail by way of non-limitative Examples.

EXAMPLE 1

(Preparation of compounds of $n=1$ and $R=C_2H_5$ in the formula (I))

30.4 Grams (1.25 mol) of metallic magnesium was introduced into a 2 l three-neck flask, and after sufficiently drying the inside of the flask by passing dry nitrogen, 50 ml of anhydrous tetrahydrofuran and a trace of iodine were added. While the resulting mixture was stirred, a solution obtained by dissolving 283.1 g (1.2 mol) of p-dibromobenzene in 600 ml of tetrahydrofuran was dropwise added to the mixture through a dropping funnel over about 1.5 hour, during which time the reaction temperature was maintained at 30° ~ 35° C. by water cooling. After the dropping, the temperature was further maintained at 30° ~ 35° C. for about 1.5 hour, to complete the formation reaction of p-bromophenylmagnesium bromide, followed by ice-cooling, thereafter dropwise adding of 128.2 g (1 mol) of 4-ethylcyclohexanone over 20 minutes, returning the temperature to room temperature, and dropwise adding a small amount of 6N hydrochloric acid to acidify the resulting solution. Said 4-ethylcyclohexanone employed in this case is the one prepared by oxidizing a commercial 4-ethylcyclohexanol with Jones reagent and having a boiling point of 87° ~ 89° C./26 mm Hg. To the above-mentioned reaction product were added 200 ml of water and 200 ml of hexane. After separating layers, the water layer was extracted with 200 ml of hexane, the hexane layers thus obtained was collected, washed with water once and the solvent was distilled off. The resulting residue was a mixture of raw cis- and trans-form 1-(p-bromophenyl)-4-ethylcyclohexanols (i.e. compounds of $R=C_2H_5$ and $n=1$ in said (A)). To this mixture was added 50 g of potassium hydrogen sulfate, and the temperature was gradually elevated under nitrogen atmosphere with stirring, and dehydration reaction was carried out by heating at 230° ~ 250° C. for 3 hours. After cooling, hexane was added to dissolve out the aimed product. After distilling off of hexane, distillation was carried out under a reduced pressure to collect a fraction having a boiling point of 126° ~ 134° C./1 mm Hg (143 g), which was then twice recrystallized from ethanol to give about 110 g of a colorless crystal of 1-(p-bromophenyl)-4-ethylcyclohexene having a melting point of 53° ~ 54° C. (a compound of $R=C_2H_5$ and $n=1$ in said (B)). 100 Grams of this compound was heated together with 41 g of cuprous cyanide in 300 ml of N-methyl-2-pyrrolidone under reflux for 4 hours, followed by distilling off about 200 ml of N-methyl-2-pyrrolidone under the atmospheric pressure, the resulting residue was treated with an aqueous solution of ferric chloride, at 60° C., then hexane-extraction, acid-washing, alkali-washing, and recrystallization from ethanol were carried out to give 52 g of colorless crystal of the objective 1-(p-cyanophenyl)-4-ethylcyclohexene (yield: 65%). This product was a monotropic liquid crystal having a C-I point (melting point) of 22° C. and a N-I point of 10° C. Further the elemental analysis values of this product showed good agreement with the theoretical values as mentioned below.

|   | Analytical values | Theoretical values (as $C_{15}H_{17}N$) |
|---|---|---|
| C | 85.1% | 85.26% |
| H | 8.2 | 8.11 |
| N | 6.5 | 6.63 |

Further NMR spectra and infrared absorption spectra of the product were not inconsistent with those of the objective compound of formula (I) ($R=C_2H_5$ and $n=1$), respectively.

EXAMPLE 2

(Preparation of a compound of $R=C_5H_{11}$ and $n=1$ in said formula (I))

236 Grams (1 mol) of p-dibromobenzene and 1 l of dry toluene were introduced into a three-neck flask in dry nitrogen atmosphere to carry out dissolution with stirring at 50° C. To the resulting solution was dropwise added 525 ml of a hexane solution of 1.67 N commercial n-butyllithium (0.88 mol), over 30 minutes. After dropping, the temperature was maintained at 50° C. further for 30 minutes, and then lowered down to 25° C. To this solution was dropwise added a solution obtained by dissolving 135 g (0.8 mol) of 4-n-pentylcyclohexanone in 125 ml of toluene, over 30 minutes, followed by continuing stirring for 30 minutes at 30° C., and then 250 ml of 6 N hydrochloric acid was added dropwise while maintaining the temperature at 30° C. or lower (the first step). The resulting organic layer was separated, 25 g of potassium hydrogen sulfate was added thereto, and after hexane was distilled off with stirring, the resulting residue was concentrated until the liquid temperature reached 110° C. to complete the dehydration reaction (the second step). The resulting concentrate was distilled under a reduced pressure to take a fraction of 160°~170° C./1 mm Hg, whereby there was obtained 160 g of 1-(p-bromophenyl)-4-n-pentylcyclohexene ($R=n-C_5H_{11}$ and $n=1$ in said formula (B)) (yield: 62.4%), which was then twice recrystallized from ethanol to give a crystal having a melting point of 67°~68° C.

Said raw material, 4-n-pentylcyclohexanone was obtained by hydrogenating p-n-pentylphenol in the presence of Raney nickel catalyst to form 4-n-pentylcyclohexanol (b.p.: 122°~130° C./10 mm Hg), and then oxidizing this material with Jones reagent (b.p. of product: 130°~134° C./22 mm Hg).

The cyanogenation reaction of the third step was carried out in the same manner as in Example 1 to give an objective product (b.p.: 153°~161° C./0.5 mm Hg) (yield: about 90%), which was then recrystallized from methanol to give a colorless objective crystal. This was a Np liquid crystal and had a C-N point of 42°~42.4° C. and a N-I point of 56.7° C. Further elemental analysis of this product accorded well with the theoretical values as mentioned below.

|   | Analytical values | Theoretical values (as $C_{18}H_{23}N$) |
|---|---|---|
| C | 85.1% | 85.32 |
| H | 9.2 | 9.15 |
| N | 5.5 | 5.53 |

Further, NMR spectra and infrared absorption spectra of this product were also not inconsistent with those of the objective product, respectively.

EXAMPLES 3~8

These Examples were carried out in the same manner as in Example 1 or Example 2 except that 4-alkylcyclohexanols employed as a raw material had an alkyl group corresponding to those of the objective products, respectively, whereby products of $n=1$ and $R=CH_3$, $n-C_3H_7$, $n-C_4H_9$, $n-C_6H_{13}$, $n-C_7H_{15}$ or $n-C_8H_{17}$ in said formula (I) were obtained. Their properties as liquid crystal are shown together with those of other compounds, in Table 1.

EXAMPLE 9

(Preparation of compound of formula (I) wherein $R=n-C_3H_7$ and $n=2$) 312 Grams (1 mol) of 4,4-dibromobiphenyl and 1.5 l of dry toluene were introduced into a 3 l three-neck flask in a dry nitrogen atmosphere, followed by stirring at 55° C. to form a solution. To this solution was dropwise added 660 ml of a hexane solution of 1.67 N commercial n-butyllithium (1.1 mol), over about 30 minutes, while the solution temperature was maintained at 50°~55° C. After cooling the resulting mixture down to 25° C., 140 g (1 mol) of 4-n-propylcyclohexanone was added dropwise while maintaining the temperature at 25°~30° C. over 30 minutes. After the addition, 50 ml of water was dropwise added with stirring at 30° C. over 30 minutes, followed by dropwise adding of 200 ml of 6N hydrochloric acid while maintaining the temperature at 30° C. or lower.

The resulting layers were separated and the lower water layer was discarded. To the upper organic layer i.e. a solution consisting mainly of 1-(4-bromobiphenylyl)-4-n-propylcyclohexanols of cis- and transforms, was added 20 g of potassium hydrogen sulfate ($KHSO_4$), followed by distilling off of the solvent by heating and concentrating until the solution temperature reached 110° C. During this period, dehydration reaction proceeded. The resulting solution while hot was transferred into an Erlenmeyer flask to precipitate said compound (B) ($R=n-C_3H_7$ and $n=2$) containing a small amount of 4,4'-dibromobiphenyl, which was then filtered and collected. A fraction of 220°~250° C./3 mm Hg was taken through vacuum distillation and recrystallization was carried out from toluene to obtain 206 g of said compound (B) ($R=n-C_3H_7$ and $n=2$) (yield: 58% based on raw material). This product was a pale yellow crystal, and melted at 165° C. to give a smetic liquid crystal, and at 235° C., it formed an isotropic liquid.

195.4 Grams (0.55 mol) of this compound (B) i.e. 1-(4'-bromo-4-biphenylyl)-4-n-propylcyclohexene, 57.5 g (0.32 mol) of cuprous cyanide, $Cu_2(CN)_2$, and 550 ml of N-methyl-2-pyrrolidone were heated together in a three-neck flask under reflux with stirring for 5 hours. 500 Ml of toluene was added thereto, the mixture was cooled, and a solution consisting of 65 g of ferric chloride, 16 ml of conc. hydrochloric acid and 750 ml of water were added and stirred for 30 minutes at 60°~70° C. The resulting two layers were separated and the resulting organic layer was washed with dilute hydrochloric acid, then with dilute aqueous sodium hydroxide, and further with water. After a small amount of solid matter was eliminated by filtration, toluene was distilled off, and vacuum-distillation was carried out to obtain 127 g of a fraction of 200°~210° C./1 mm Hg as a crude compound (I) (R=n-C$_3$H$_7$ and n=2) (yield: 76% based on said compound (B)), which was then further dissolved in toluene. After the resulting solution was passed through an alumina layer for chromatography, the toluene solution was concentrated and recrystallized to give 105 g of purified compound (I) i.e. 1-(4-cyano-4-biphenylyl)-4-n-propylcyclohexene. This product had a melting point (C-N point) of 110° C. and a clear point (N-I point) of 232° C., and elemental analysis of this product accorded well with the calculated values as mentioned below.

|   | Analytical values | Calculated values (as C$_{22}$H$_{23}$N) |
|---|---|---|
| C | 87.5% | 87.66% |
| N | 7.7% | 7.69% |

Further, infrared absorption spectra of this product were not inconsistent with those of the objective compound.

In addition, the 4-propylcyclohexanone employed as a raw material in this preparation example was prepared as follows: A commercial p-n-propylphenol was hydrogenated in the presence of ethanol, sodium ethoxide and Raney nickel catalyst, under a hydrogen pressure of 100 atm, at 150° C. to form 4-n-propylcyclohexanol, which was then oxidized with Jones reagent (CrO$_3$/H$_2$SO$_4$/H$_2$O) in acetone to obtain 4-n-propylcyclohexanone having a b.p. of 110°∼113° C./26 mm Hg.

EXAMPLES 10∼12

Example 9 was repeated except that 4-n-propylcyclohexanone as a raw material in Example 9 was replaced by 4-methyl-, 4-n-C$_4$H$_9$- or 4-n-C$_5$H$_{11}$-cyclohexanone, to obtain compounds of R=CH$_3$, n-C$_4$H$_9$ or n-C$_5$H$_{11}$ and n=2, respectively, in said formula (I). Their properties as liquid crystal are shown together with other compounds in Table 1.

EXAMPLE 13 (Application example 1)

A mixture of 1-(p:cyanophenyl)-4-n-pentylcyclohexene obtained in Example 2, and 1-(p-cyanophenyl)-4-n-heptylcyclohexene obtained in Example 7, in a mixing proportion by weight of 1:1, is a nematic liquid crystal having a positive dielectric anisotropy (Np liquid crystal) at room temperature and forms an isotropic liquid at 59° C. The viscosity of this mixture is 36 cp at 25° C. which is a much lower value than those of conventional liquid crystal compositions. The mixture was sealed in a twisted nematic type liquid crystal cell having a thickness of 10 μm, and its actuation threshold voltage was measured to give 1.8 V, and its saturation voltage was 3.0V.

EXAMPLE 14 (Application example 2)

A liquid crystal mixture consisting of 23 parts of 1-(p-cyanophenyl)-4-n-ethylcyclohexene obtained in Example 1, 38.5 parts of 1-(p-cyanophenyl)-4-n-pentylcyclohexene obtained in Example 2 and 38.5 parts of 1-(p-cyanophenyl)-4-n-heptylcyclohexene obtained in Example 7, has a liquid crystal temperature range of −15° to 48° C. Further, its viscosity at 25° C. has as low a value as 25 cp. A twisted nematic type liquid crystal cell of 8.5 μm thick was constructed employing said mixture and its actuation threshold voltage was measured to give 1.5 V, and its actuation saturation voltage was 2.2 volt. Further, its response time was so short as a rise time of 70 m sec. and a decay time of 50 m sec. at 25° C., while even in case of 0° C., the rise time and the decay time were 500 m sec. and 250 m sec., respectively. Accordingly when this liquid crystal mixture is employed, it is possible even at 0° C., to effect an of-off actuation for display of second. Such a short response time is due to the low viscosity of this liquid crystal mixture.

EXAMPLE 15 (Application example 3)

A liquid crystal mixture consisting of 17 parts of 1-(p-cyanophenyl)-4-n-pentylcyclohexene obtained in Example 2, and 17 parts of 1-(p-cyanophenyl)-4-n-heptylcyclohexene, 24 parts of 4-methoxy-4'-ethylazoxybenzene and 42 parts of 4-methoxy-4'-n-butylazoxybenzene, obtained in Example 7 did not crystallize even at −20° C. and maintained a liquid crystal state up to 68° C. The twisted nematic type liquid crystal cell having a thickness of 10 μm wherein the above-mentioned liquid crystal mixture was employed had an actuation threshold voltage of 2.5 V and an actuation saturation voltage of 3.5 V. This liquid crystal mixture can be suitably employed as a liquid crystal for multiplex driving.

EXAMPLE 16 (Application example 4)

A liquid crystal composition having the following proportion of compounds was prepared:

| | |
|---|---|
| 1-(p-cyanophenyl)-4-propylcyclohexene (wherein R = n-C$_3$H$_7$, n = 1 in formula (I)) | 0.38 mol |
| 1-(p-cyanophenyl)-4-pentylcyclohexene (wherein R = n-C$_5$H$_{11}$, n = 1 in formula (I)) | 0.29 mol |
| 1-(p-cyanophenyl)-4-hexylcyclohexene (wherein R = n-C$_6$H$_{13}$, n = 1 in formula (I)) | 0.16 mol |
| 1-(p-cyanophenyl)-4-heptylcyclohexene (wherein R = n-C$_7$H$_{15}$, n = 1 in formula I)) | 0.12 mol |
| 1-(4-cyano-4-biphenylyl)-4-n-propylcyclohexene (wherein R = n-C$_3$H$_7$, n = 2 in formula (I)) | 0.043 mol |

This liquid crystal composition had a clear point of 60° C., and even when it was preserved at −10° C. over several months, no crystal precipitated. Further the viscosity of this liquid crystal composition was 35 cp at 25° C. This composition was sealed into a twisted nematic type liquid crystal cell having a thickness of 10 μm and its actuation threshold voltage and its actuation saturation voltage were measured to give values of 1.5 V and 2.2 V, respectively. Further as for the response time, the rise time and the decay time were 90 m sec. and 70 m sec., respectively (measured at 3 V, 32 Hz, 25° C.).

EXAMPLE 17 (Application example 5)

A liquid crystal composition having the following mixing proportion of compounds was prepared:

| | |
|---|---|
| 1-(p-cyanophenyl)-4-propylcyclohexene | 0.45 mol |
| 1-(p-cyanophenyl)-4-n-pentylcyclohexene | 0.34 mol |
| 1-(p-cyanophenyl)-4-n-heptylcyclohexene | 0.16 mol |
| 1-(p-cyano-4-biphenylyl)-4-n-propylcyclohexene | 0.053 mol |

The resulting composition had a clear point of 61° C., and the lower limit of its nematic temperature range was −4° C. Further its viscosity was 35 cp at 25° C. This composition was sealed into a twisted nematic type liquid crystal cell having a thickness of 9.5 μm and its actuation threshold voltage and its actuation saturation voltage were measured to give values of 1.5 V, 2.2 V, respectively. Further as for the response time, the rise time and the decay time were 90 m sec. and 75 m sec., respectively (measured at 25° C., 3 V, 32 Hz).

EXAMPLE 18 (Application example 6)

A liquid crystal composition having the following proportion of compounds was prepared:

| | |
|---|---|
| 1-(p-cyanophenyl)-4-n-propylcyclohexene | 0.32 mol |
| 1-(p-cyanophenyl)-4-n-butylcyclohexene | 0.26 mol |
| 1-(p-cyanophenyl)-4-n-pentylcyclohexene | 0.23 mol |
| 1-(p-cyanophenyl)-4-n-heptylcyclohexene | 0.094 mol |
| 1-(4-cyano-4-biphenylyl)-4-methylcyclohexene | 0.029 mol |
| 1-(4-cyano-4-biphenylyl)-4-n-propylcyclohexene | 0.034 mol |
| 1-(4'-cyano-4-biphenylyl)-4-n-butylcyclohexene | 0.029 mol |

The resulting composition had a clear point of 78° C., and even when it was preserved at −10° C. over several months, no crystal precipitated. This composition was sealed in a twisted nematic type liquid crystal cell having a thickness of 10 μm and its actuation characteristics were measured to give an actuation threshold voltage at 25° C., of 1.4 V and an actuation saturation voltage at 25° C., of 2.2 V, respectively. Further, as for the response time, its rise response time and decay response time were 110 m sec. and 90 m sec., respectively (measured at 25° C., 3V, 32 Hz).

EXAMPLE 19 (Application example 7)

A liquid crystal mixture consisting of
15 parts by weight of 4,4'-di-n-butylazoxybenzene,
23 parts by weight of 4-methoxy-4'-ethylazoxybenzene
and 47 parts by weight of 4-methoxy-4'-n-butylazoxybenzene,
has a negative dielectric anisotropy, and hence cannot be employed for a twisted nematic type liquid crystal cell. Whereas a liquid crystal composition obtained by further adding thereto
8 parts of 1-(4'-cyano-4-biphenylyl)-4-n-propylcyclohexene
and 8 parts of 1-(4'-cyano-4-biphenylyl)-4-n-pentylcyclohexene
of formula (I) of the present invention, has a positive dielectric anisotropy, and does not crystallize even at −15° C., and maintains its nematic state up to 93° C. Employing this liquid crystal composition, a twisted nematic type liquid crystal cell having a clearance thickness of 9.5 μm was constructed and its actuation characteristics were measured, whereby an actuation threshold voltage of 2.5 V and an actuation saturation voltage of 3.4 V were obtained. This liquid crystal composition can be suitably employed as a liquid crystal for multiplex driving.

EXAMPLE 20 (Application example 8)

A liquid crystal composition consisting of
4-n-pentyl-4'-cyanobiphenyl (11 parts),
4-n-heptyl-4'-cyanobiphenyl (27 parts),
4-n-octyloxy-4'-cyanobiphenyl (16 parts) and
1-(4'-cyano-4-biphenylyl)-4-n-propylcyclohexene (11 parts) has a nematic liquid crystal temperature range of −15° C. to +62° C. and a viscosity at 25° C. of 45 cp. This composition was sealed into a twisted nematic type liquid crystal cell having a thickness of 10 μm and its actuation threshold voltage and its actuation saturation voltage were measured to give values of 1.5 V and 2.2 V, respectively. Further its rise response time and decay response time were 90 m sec. and 90 m sec., respectively (measured at 3 V, 32 Hz, 25° C.).

EXAMPLE 21 (Application example 9)

A liquid crystal composition consisting of
4-n-propylcyclohexyl-4'-cyanobenzene (34 parts),
4-n-pentylcyclohexyl-4'-cyanobenzene (34 parts),
4-n-heptylcyclohexyl-4'-cyanobenzene (22 parts) and
1-(4'-cyano-4-biphenylyl)-4-n-propylcyclohexene (10 parts)
has a nematic liquid crystal temperature range of −10° C. to +68° C., and its viscosity at 25° C. of 25 cp. This liquid crystal composition was sealed in a twisted nematic type liquid crystal cell having a thickness of 10 μm and actuation threshold voltage, and actuation saturation voltage of this cell were measured to give 1.5 V and 2.4 V, respectively. Further its rise response time and decay response time were 110 m sec. and 60 m sec., respectively (measured at 3 V, 32 Hz, 25° C.).

What is claimed is:

1. 4-Alkylcyclohexenes having at the 1-position thereof p-cyanophenyl group or 4'-cyano-4-biphenylyl group, expressed by the general formula

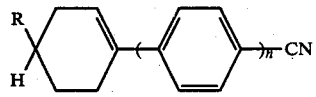

wherein R represents a straight alkyl group having 1~9 carbon atoms and n represents 1 or 2.

2. 1-(p-Cyanophenyl)-4-alkylcyclohexenes expressed by the general formula

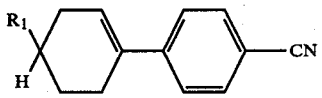

wherein $R_1$ represents a straight alkyl group having 3~7 carbon atoms.

3. 1-(4'-Cyano-4-biphenylyl)-4-alkylcyclohexenes expressed by the general formula

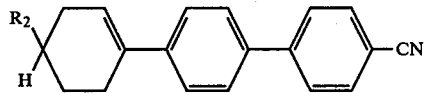

wherein $R_2$ represents a straight alkyl group having 3~5 carbon atoms.

4. A method for producing 1-(p-cyanophenyl)-4-alkylcyclohexenes expressed by the general formula

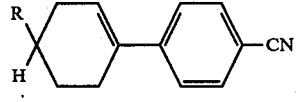

wherein R represents a straight alkyl group having 1~9 carbon atoms, which method comprises:
reacting a 4-alkylcyclohexanone (wherein the alkyl group has a straight chain of 1~9 carbon atoms) with p-bromophenylmagnesium bromide or p-bromophenyllithium to form a mixture of cis- and trans-forms of 1-(p-bromophenyl)-4-alkylcyclohexanols (the first step);
subjecting said mixture of cis- and trans-forms, as it is, to a dehydration reaction to form a 1-(p-bromophenyl)-4-alkylcyclohexene (the second step); and replacing the Br group of the compound thus prepared by cyano group (the third step).

5. A method for producing 1-(4'-cyano-4-biphenylyl)-4-alkylcyclohexenes expressed by the general formula

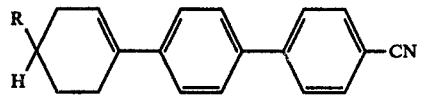

wherein R represents a straight alkyl group having 1~9 carbon atoms, which method comprises:
reacting a 4-alkylcyclohexanone (wherein the alkyl group has a straight chain of 1~9 carbon atoms) with 4-bromo-4'-biphenyllithium to prepare a mixture of cis- and trans-forms of 1-(4'-bromo-4-biphenylyl)-4-alkylcyclohexanols (the first step);
subjecting said mixture of cis-and trans-forms to a dehydration reaction to form a 1-(4'-bromo-4-biphenylyl)-4-alkylcyclohexene (the second step); and replacing the Br group of the compound thus prepared by cyano group (the third step).

6. A nematic liquid crystal composition containing at least one member selected from the group consisting of 1-(p-cyanophenyl)-4-alkylcyclohexenes and 1-(4'-cyano-4-biphenylyl)-4-alkylcyclohexenes, expressed by the general formula

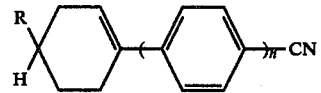

wherein R represents a straight alkyl group having 1~9 carbon atoms and n represents 1 or 2.

* * * * *